United States Patent [19]

Zimlich, Jr. et al.

[11] Patent Number: 5,288,647
[45] Date of Patent: Feb. 22, 1994

[54] METHOD OF IRRADIATING BIOLOGICAL SPECIMENS

[75] Inventors: William C. Zimlich, Jr.; Joseph A. Sorge, both of San Diego, Calif.

[73] Assignee: Stratagene, La Jolla, Calif.

[21] Appl. No.: 686,491

[22] Filed: Apr. 17, 1991

Related U.S. Application Data

[62] Division of Ser. No. 189,285, May 2, 1988, abandoned.
[51] Int. Cl.$^5$ ............................................. G01J 1/04
[52] U.S. Cl. .................................... 436/174; 204/193; 250/372; 250/455.11; 250/504 R; 250/492.1; 356/51; 356/72; 364/188; 364/189; 364/413.26; 422/186.3; 435/291
[58] Field of Search ................ 422/186.3, 186.07, 186, 422/24; 436/174; 204/193; 250/372, 455.1, 492.1, 504 R; 435/6, 291; 536/27; 427/8, 10; 364/413.26, 188, 189; 356/51, 72

[56] References Cited

U.S. PATENT DOCUMENTS

| | | | |
|---|---|---|---|
| 3,491,234 | 1/1970 | Wiltrout | 422/24 |
| 3,852,032 | 12/1974 | Urbach | 422/24 |
| 4,279,254 | 7/1981 | Boschetti et al. | 128/395 |
| 4,400,270 | 8/1983 | Hillman | 422/28 X |
| 5,180,611 | 1/1993 | Costello | 427/96 |

OTHER PUBLICATIONS

Church et al, *Proc. Nat'l. Acad. Sci. USA*, vol. 81, pp. 1991-1995, Apr. 1984.

*Primary Examiner*—Robert J. Warden
*Assistant Examiner*—Amalia Santiago
*Attorney, Agent, or Firm*—Lyon & Lyon

[57] ABSTRACT

A method of irradiating a biological specimen with ultraviolet, in particular a polynucleotide specimen selected from DNA or RNA, or optionally a protein. In the case where the specimen is DNA or RNA, or potentially proteins, the specimen is irradiated to cross-link the specimen to a substrate. In the case where the specimen is DNA, the specimen can also be irradiated to form thymine dimers. The method uses an apparatus which permits relatively precise control of the total ultraviolet dose received by the specimen, despite any changes of ultraviolet flux from the lamps which may occur from during any one experiment, or between a number of experiments. Thus, the method allows relatively highly reproducible results to be obtained.

6 Claims, 10 Drawing Sheets

| fig.4A. | fig.4D. |
| --- | --- |
| fig.4B. | fig.4C. |

| fig.5A. | fig.5D. |
| --- | --- |
| fig.5B. | fig.5C. |

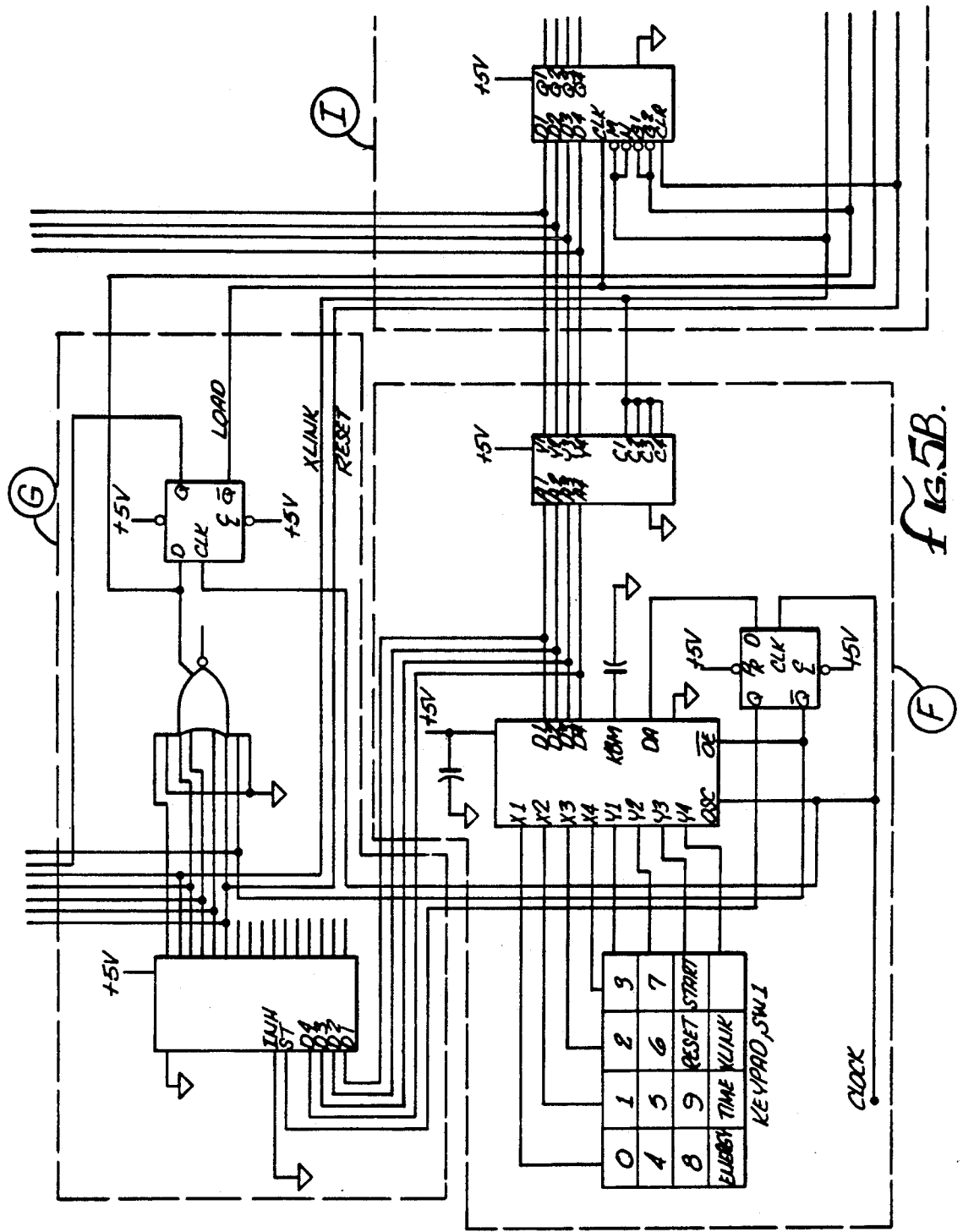

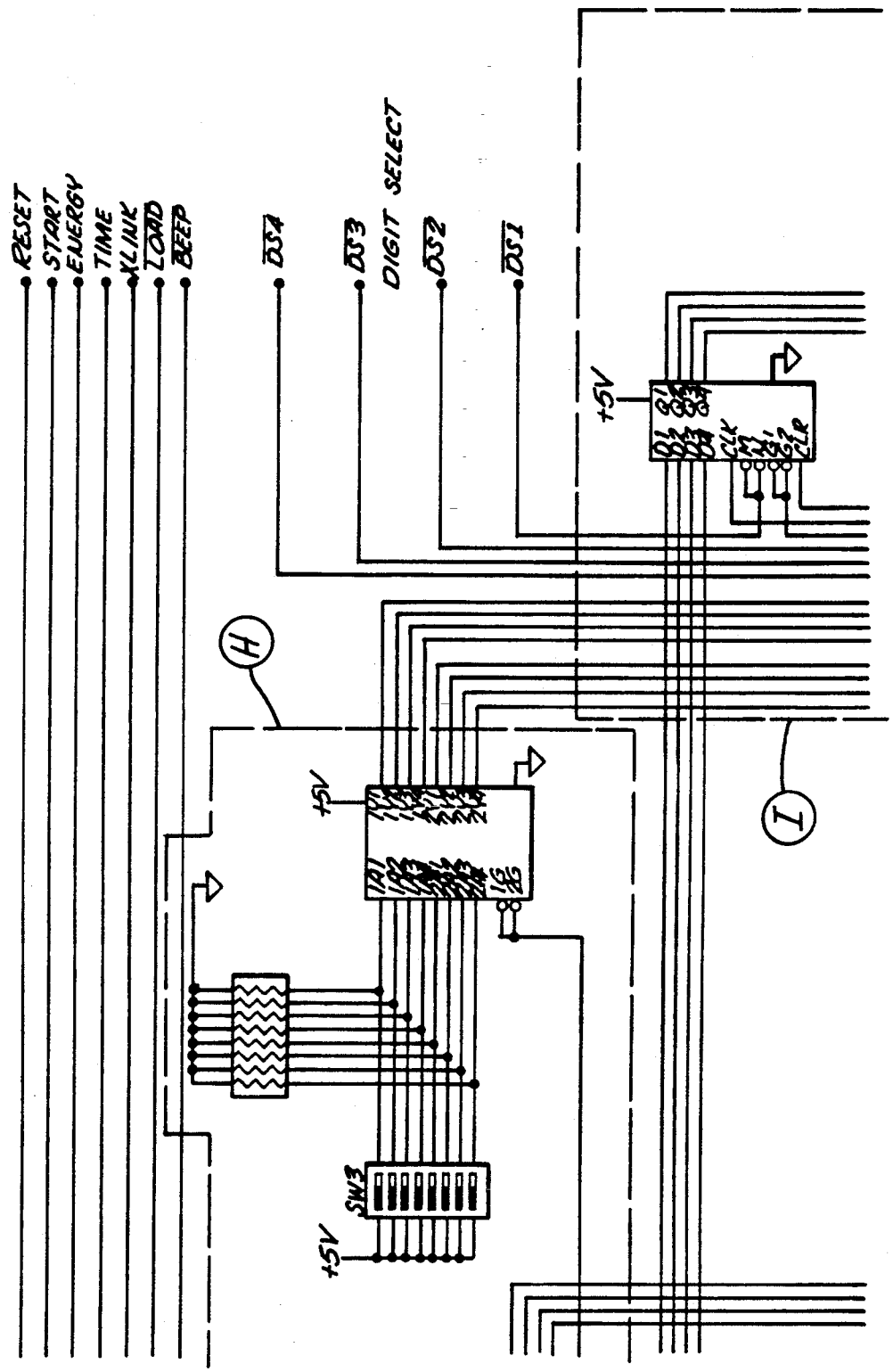

METHOD OF IRRADIATING BIOLOGICAL SPECIMENS

This is a divisional application of Ser. No. 189,285 filed May. 2, 1988, now abandoned, by hereby incorporated by reference as if fully set forth herein.

FIELD OF INVENTION

This invention relates to a method by which polynucleotide specimens (DNA or RNA), can be relatively automatically and safely irradiated, particularly for the purpose of fixing them to a substrate, and in the case of DNA also forming thymine dimers.

BACKGROUND

A common technique for sequencing DNA is the Southern blot. This technique involves transferring DNA fragments from agarose gels to a membrane, typically to a nitrocellulose membrane. The DNA fragment would then be hybridized with labeled complimentary DNA probes. More recently, various nylon membranes have been used in place of nitrocellulose, since nylon membranes generally bind DNA thereto better than nitrocellulose. Furthermore, it has also been found that DNA binding to a nylon or nitrocellulose membrane, could be considerably enhanced if the DNA fragments, following placement on the membrane, were irradiated with ultraviolet light ("UV") at a peak emission of 254 nanometres ("nm"). Such a technique has been described by Kandjian, *Biotechnology*, Vol. 5, p. 165-167 (February, 1987), as well as by Church et al., *Proc. Natl. Acad. Sci. USA*, Vol. 81, p. 991-995 (April, 1984). The enhanced DNA binding to the substrate permits any initial probe/DNA hybrids to be denatured, and the bound DNA fragments reprobed many times with probes of different sequences, without any significant loss of signal from any hybrids formed. Thus, the overall sensitivity of the Southern blot technique is enhanced.

It has also been recently known to irradiate DNA with 254 nm UV to form thymine dimers. Thymine dimer formation results in only partial digestion of a DNA specimen upon exposure to a restriction enzyme, and thereby facilitates restriction site mapping of the specimen. Formation of thymine dimers by UV irradiation, with subsequent restriction site mapping, is described by Whittaker et al., *Gene*, Vol. 41, p. 129-134 (1986), and by Cleaver, *Biochimica Et Biophysica Acta*, Vol. 697, p. 255-258 (1982). Furthermore, as suggested by Saito et al., *Tetrahedron Letters*, Vol 22, No. 34, pp. 3265-3268 (1981), 254 nm UV can also been used to irradiate thymine in the presence of primary amines, to produce N(1)—substituted thymines.

In practice, the above techniques are typically performed by an improvised arrangement, using one or more ultraviolet lightbulbs positioned in some convenient location in the laboratory, such as a fumehood or lab benchtop. The DNA specimens (typically on a substrate) would simply be placed an appropriate distance from the UV lights such that the UV flux on the DNA is approximately that desired, and the lights manually energized and de-energized following elapse of an appropriate time.

There are several difficulties associated with the foregoing procedure. First, the extent to which any reaction occurs, for example, cross-linking of DNA to a substrate or formation of thymine dimers, is dependent upon the total energy received by the DNA specimen. This is a function of the UV flux received by the specimen at any given time, over the total time of exposure. However, the flux of a UV light source, typically a low pressure mercury lamp, is not constant over the life of the source. Furthermore, previously typically more than 1 UV lamp was used simultaneously to irradiate the DNA specimen. Should a total or partial failure occur in one of the lamps, the total flux received by the specimen would drop by an unknown quantity. The foregoing factors, which lead to variations in flux received by a DNA specimen either over a given experiment, or from experiment to experiment, lead to a lack of accurately reproducible results. Another difficulty with the previously improvised method, at least in the case where the DNA was to be cross-linked to a substrate, was that often a laboratory technician would at best roughly guess the flux from the UV light source to be used, and then additionally roughly guess the time of exposure required to supply the required total energy (which may be available from a reference, but was typically also estimated). This again led to results which were not accurately reproducible. Furthermore, the typical improvised arrangement, could likely result in UV leakage. The dangers of shortwave UV are well known, and thus prior arrangements could result in hazardous UV exposure to laboratory workers.

SUMMARY OF THE INVENTION

The present invention provides a method of irradiating a polynucleotide specimen, typically for the purpose of cross-linking it to a substrate, or at least in the case of DNA, for alternatively forming thymine dimers. The term "polynucleotide" refers to either deoxyribonucleotide ("DNA") or ribonucleotide ("RNA"). The method of the present invention uses an apparatus suitable for irradiating polynucleotide specimens with an accurate amount of total UV dose, the accuracy of which is not affected by a decrease in output from one or more ultraviolet lamps, so as to enhance the reproduceability of experimental results either during a given experiment, or from experiment to experiment. The apparatus further provides a means by which a predetermined total energy can be provided to a polynucleotide specimen for reliable cross-linking to a substrate, or for thymine dimer formation. Alternatively a fixed total UV dose can be selected, or if desired, simply a time of exposure can be selected. The apparatus further substantially eliminates any shortwave UV exposure hazard to laboratory workers.

The method of the present invention then, involves irradiating a polynucleotide specimen, or optionally a protein specimen, with ultraviolet ("UV"), using an apparatus comprising a housing with a repository for the specimen. An ultraviolet lamp fixture is fitted within the housing, which fixture receives at least one, and preferably a plurality, of ultraviolet lamps to illuminate the repository and hence any specimens placed thereon. An energy detector provides an indication of the total ultraviolet dose received on the repository at any time. A control is linked to the foregoing detector, and to the lamp receptacle. This control can de-energize the lamp fixture upon detection of a selected or predetermined total ultraviolet dose by the energy detector. Preferably, the control will de-energize the lamp fixture upon detection of a predetermined ultraviolet dose of between approximately 1.0 to 2.0 kiloJoules per square meter ($KJ/m^2$), and preferably approximately 1.29

KJ/m². The dose of 1.29 KJ/m² is preferably provided by a UV flux (i.e. intensity) of about 4300 microwatts/cm² for approximately 30 seconds.

A timer (the setting of which can be varied) is optionally provided, which is linked to the lamp receptacle. This timer can also de-energize the lamp fixture upon a lapse of a selected period during which the lamp fixture is energized.

The energy detector preferably has a sensor, typically in the form of a photosensor, which provides a signal corresponding to the ultraviolet flux on the repository. A detector circuit, which is also a part of the energy detector, is connected to the foregoing sensor. This detector circuit provides an indication of the total ultraviolet dose received on the repository based upon the signal which was received from the sensor over time.

The control circuit comprises at least one of a variable memory or a fixed memory, and preferably both. The fixed memory retains a fixed, predetermined value corresponding to a predetermined quantity of energy. The variable memory on the other hand, allows for selection of a variable value corresponding to a selected quantity of energy. By a fixed, first value is meant that this value either cannot be changed after the apparatus has been assembled, or if it can, it cannot be changed by the same means as the variable value and in fact is more difficult to change. Typically, if the fixed value can be changed, the access to the means for changing it is limited in that such means is disposed in an enclosed housing, or special tools are required to manipulate such means. Furthermore, the fixed value is retained in the fixed memory even if the apparatus is turned off, or unplugged from an external power source. In the preferred case where the control circuit has both fixed and variable memories, a memory switch is additionally provided which can select either of the foregoing memories. Thus, by positioning the memory switch as desired, the control circuit will deenergize the lamp fixture upon detection of either the selected or the predetermined UV dose.

In the preferred practice of the method, an apparatus is used in which the housing is substantially opaque to ultraviolet light, and in addition to the repository, has a door which allows for access to an interior of the housing. This embodiment is additionally provided with a keypad (which term as used in this application, includes suitable switches, either pushbutton, dial, or any other type) on the outside of the housing and which is connected to the control circuit. The keypad carries the memory switch previously mentioned, as well as keys by which the variable value in the variable memory can be selected. Additionally, a preferred feature, is a safety switch which de-energizes the lamp fixture (assuming of course, that the lamp fixture is already energized), upon opening of the door. By such means, inadvertent exposure of an operator to the shortwave UV within the chamber, is avoided.

In the practice of the method of the invention, the specimen is placed into the repository in the housing, and the operator then uses the keypad to select whether the timer will deenergize the UV lamp receptacle, or whether the fixed memory or variable memory of the control circuit will result in deenergizing of the UV lamp receptacle. In the event that a selected value of the variable memory, or the timer, will be used to deenergize the receptacle, then the corresponding values are entered into the keypad. The lamp fixture is then energized, preferably by a start switch also located on the keypad. Of course, if the apparatus includes the preferred safety switch, then the door must first be closed before the lamp fixture can be energized.

An apparatus suitable for use in the practice of the method of the present invention, is also provided.

DRAWINGS

Embodiments of the invention will now be described with reference to the accompanying drawings in which:

FIGS. 4A to 4D are overlapping portions of a part of the circuitry of the apparatus of FIGS. 1-3;

FIGS. 5A, 5B, 5C and 5D are put together into a single drawing;

FIGS. 5A to 5D are overlapping portions of a second part of the circuitry of the apparatus of FIGS. 1-3.

DETAILED DESCRIPTION OF EMBODIMENTS OF THE INVENTION

Figure 1:
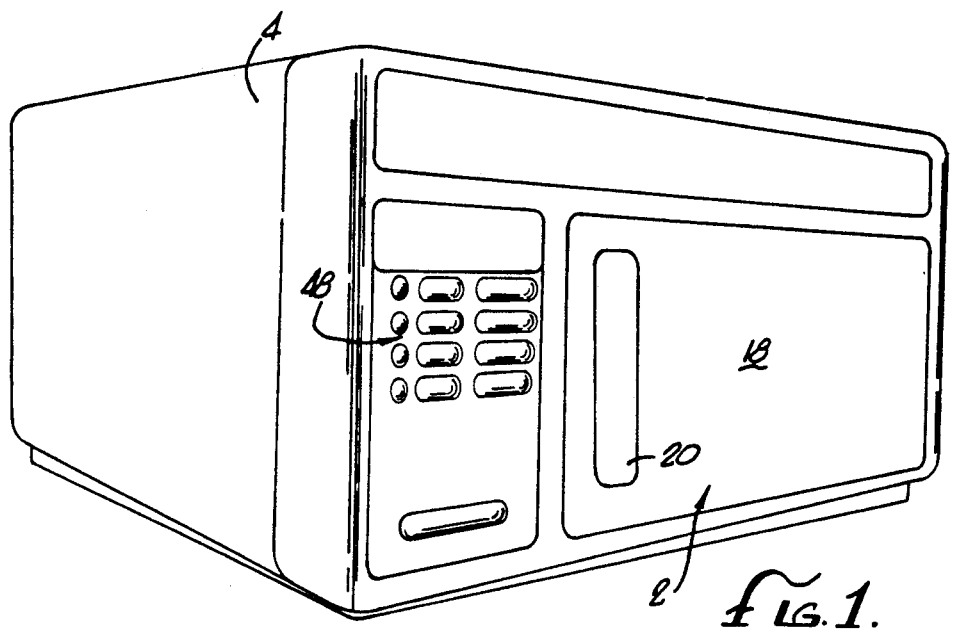
FIG. 1 is a perspective view of a UV irradiating apparatus suitable for practicing the method of the present invention.
Figure 2:
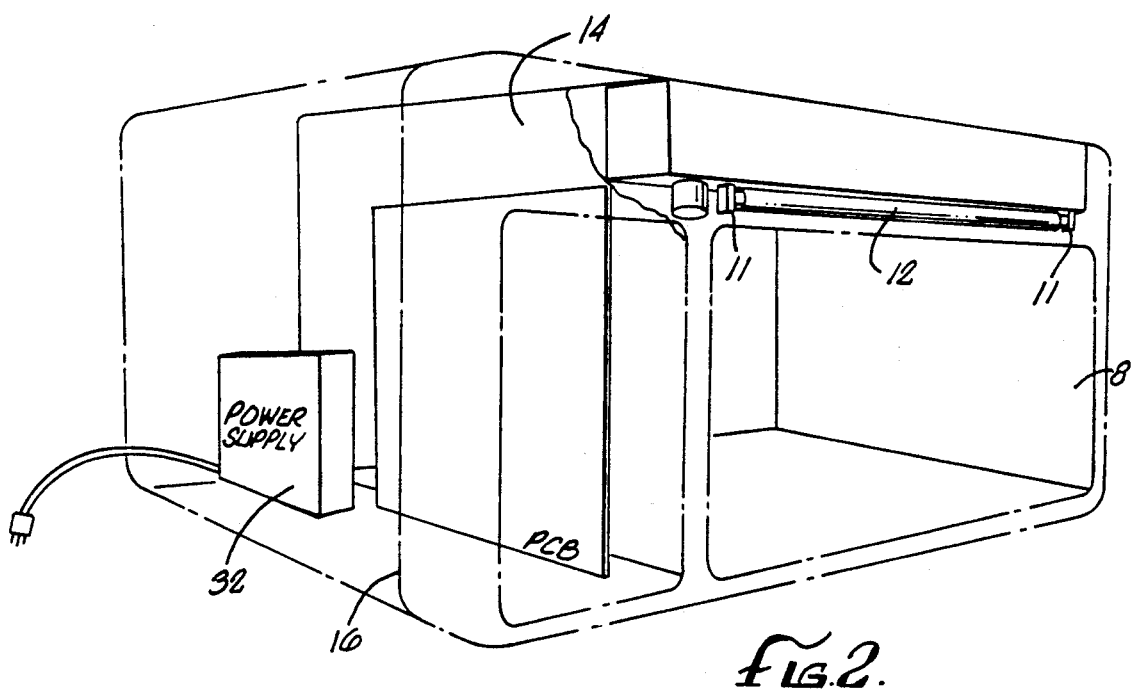
FIG. 2 is a view of the apparatus of FIG. 1, which view is similar to that of FIG. 1 except with portions cut away to reveal interior components thereof.

Referring to the drawings, the UV irradiating apparatus which is used in the practice of the present invention, is generally numbered 2, and has a substantially UV opaque chamber 8 which is essentially closed. However, chamber 2 is accessible through door 18 by gripping handle 20. A lower surface 9 of chamber 8 acts as a repository for a specimen, preferably a polynucleotide, which is typically disposed on a substrate. A lamp fixture 10, in the form of five pairs of lamp sockets 11 (only one pair of which is shown in FIG. 2), is disposed on an upper side of chamber 8. Each pair of opposed sockets 11 is designed to receive well known elongated low pressure mercury UV lamps, such as lamp 12 illustrated in FIG. 2, preferably one which has a maximum intensity of emission of 254 nm. Chamber 8 is surrounded by a outer housing 4 to form a compartment 16 in which is carried the electronic circuits of apparatus 2.

Figures 3, 4, 5:
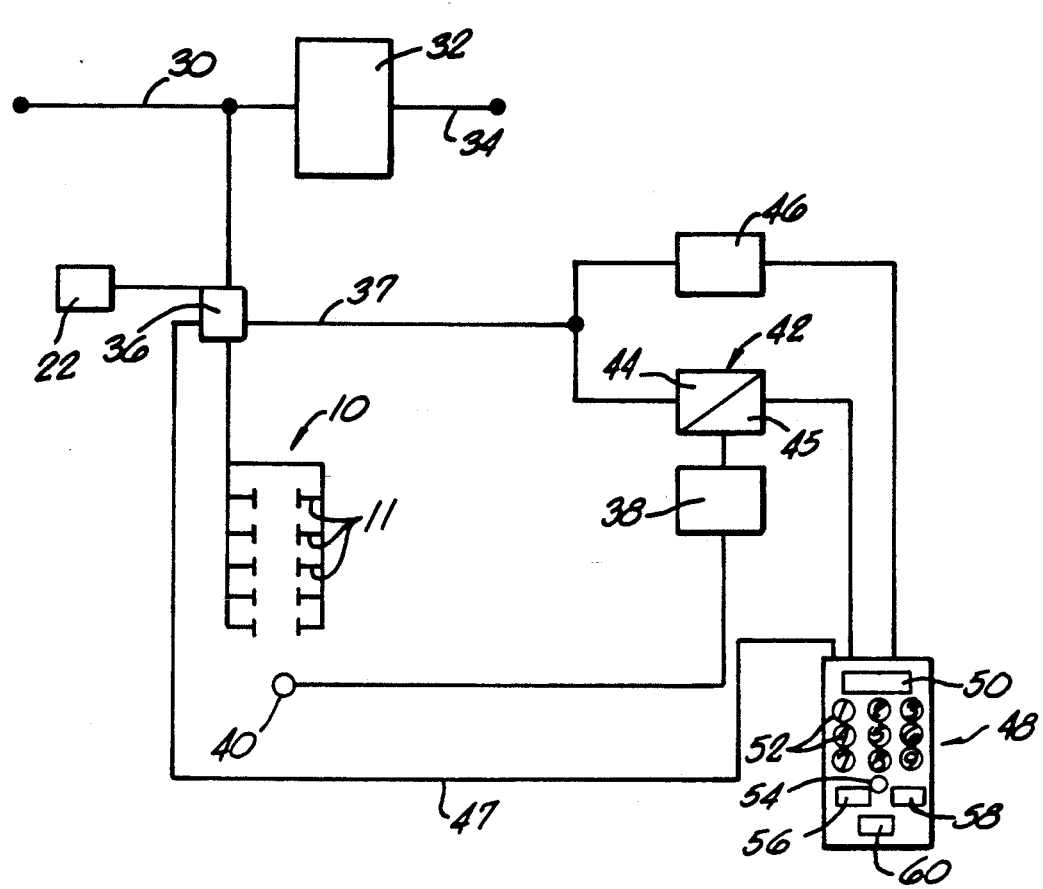
FIG. 3 is a block diagram illustrating the circuitry used in the apparatus of FIGS. 1 and 2.
FIG. 4 shows how
FIG. 5 shows how
Figure 4A:
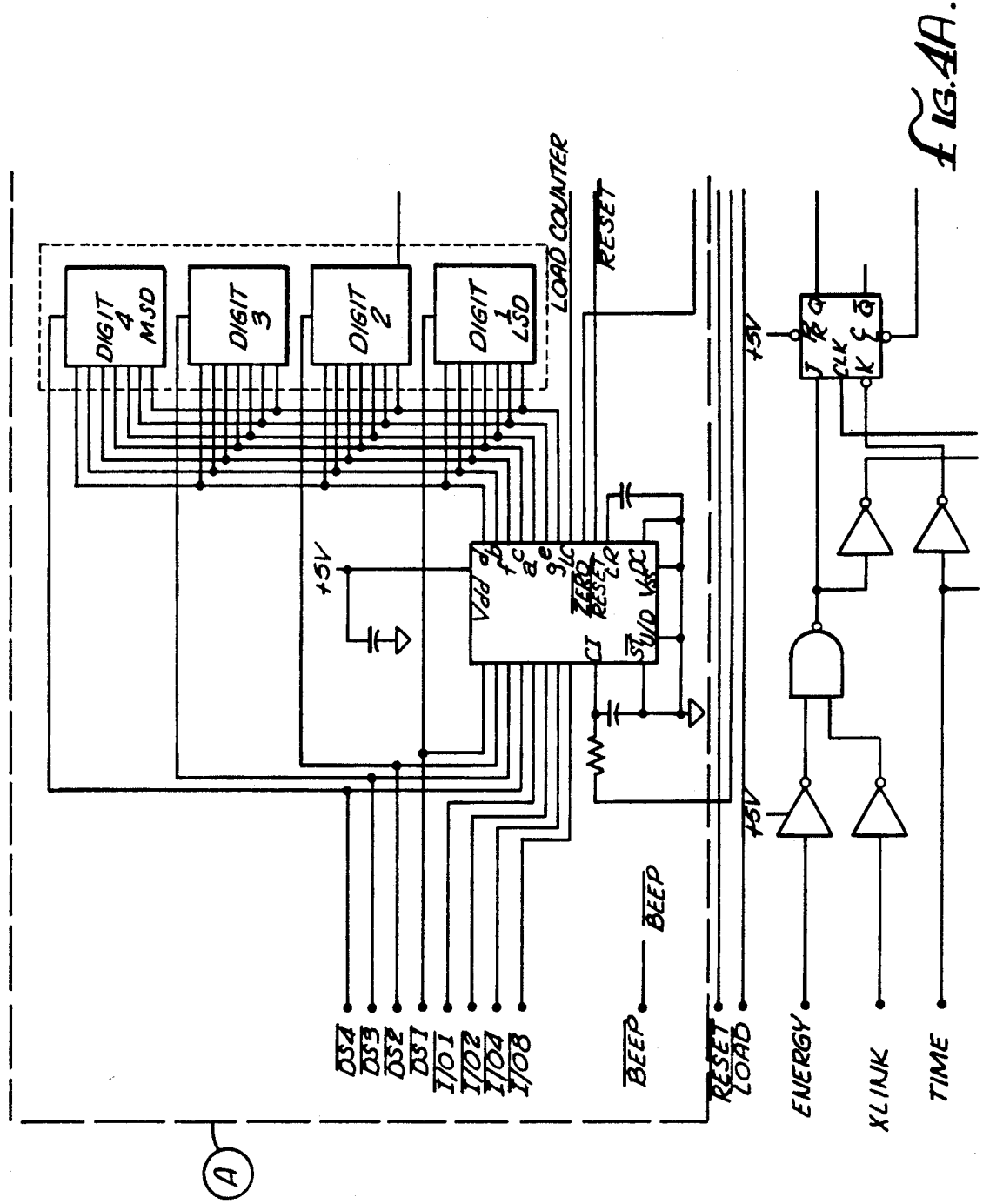
FIGS. 4A, 4B, 4C and 4D are put together into a single drawing.
Figure 4B:
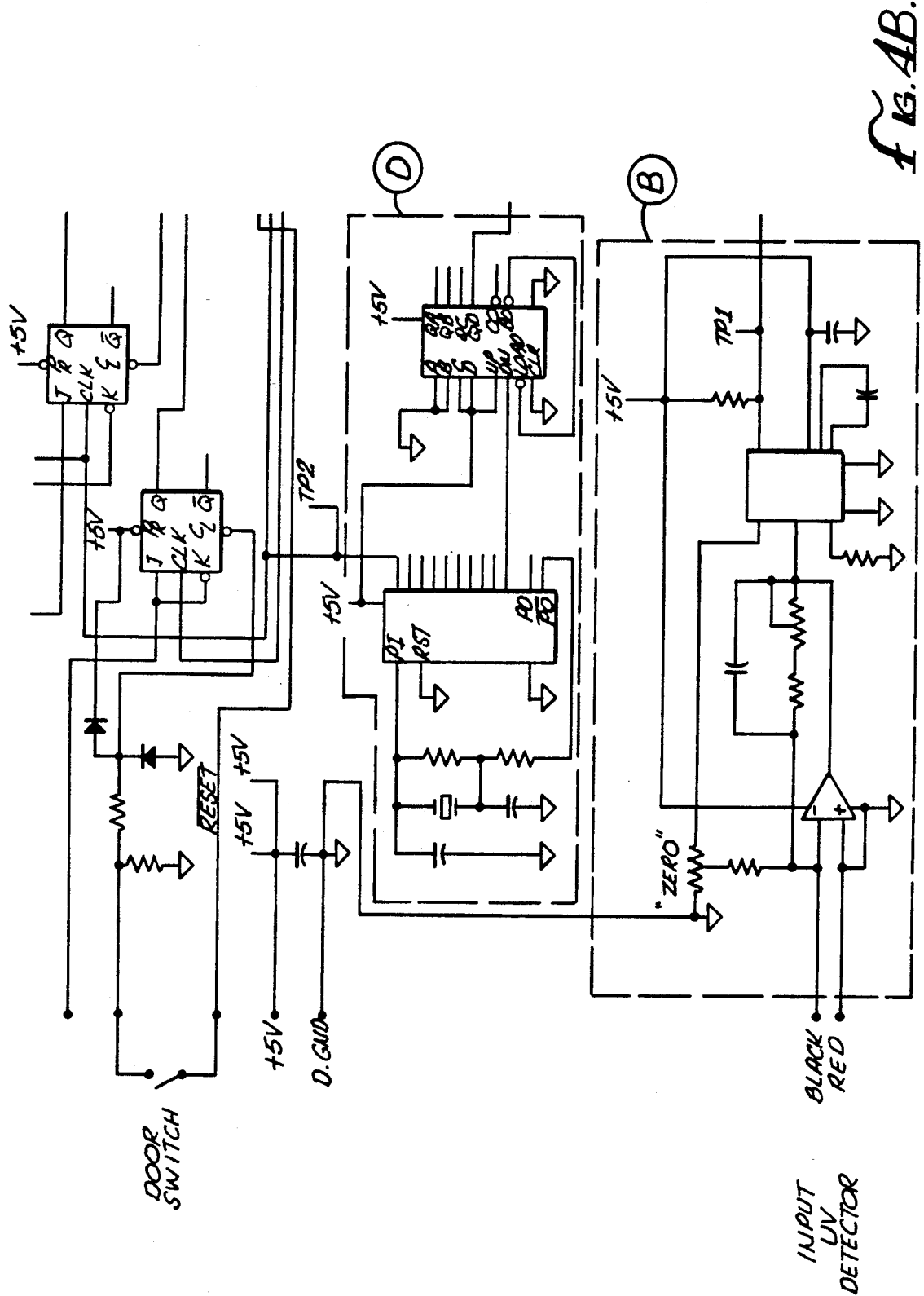
Figure 4C:
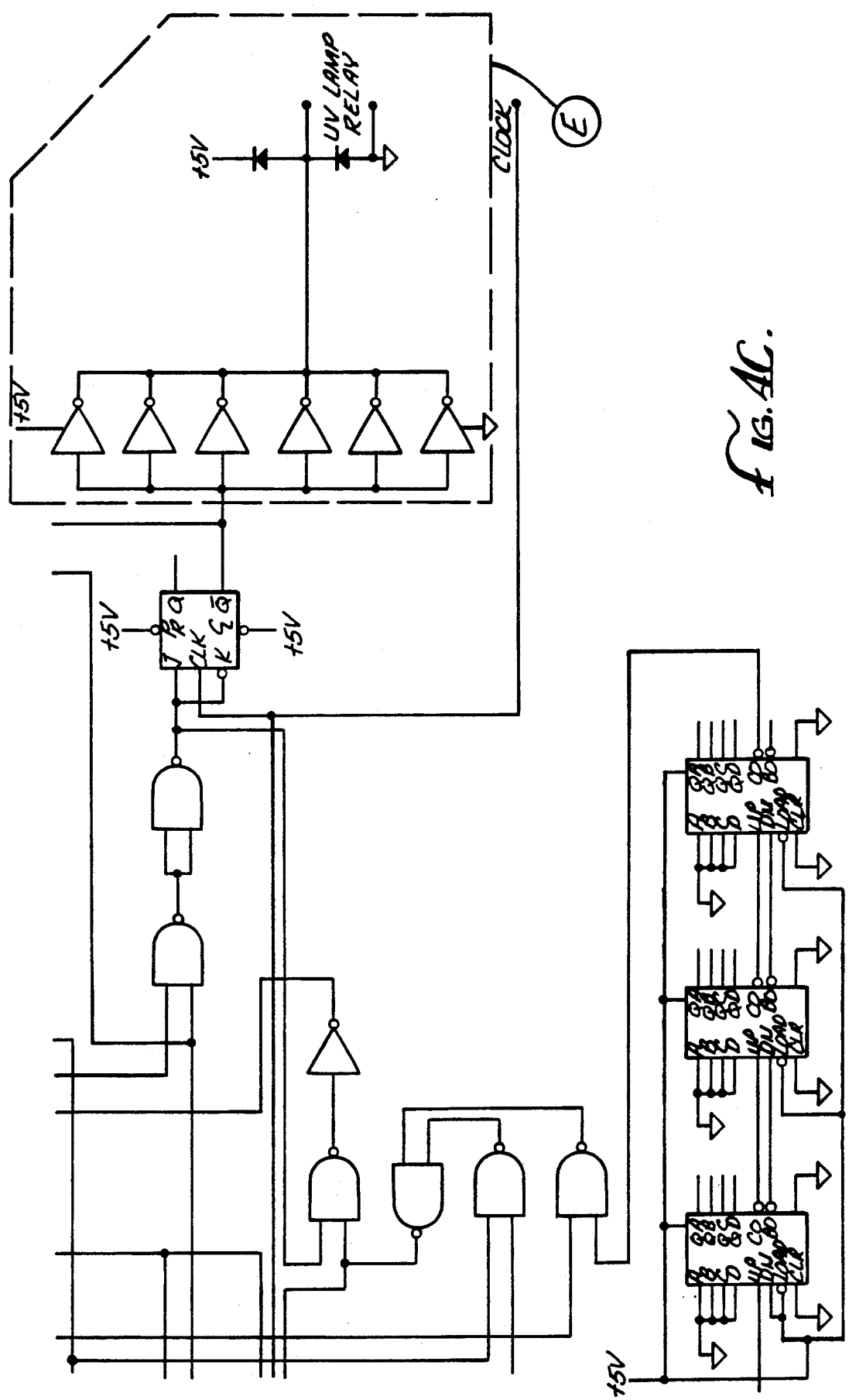
Figure 4D:
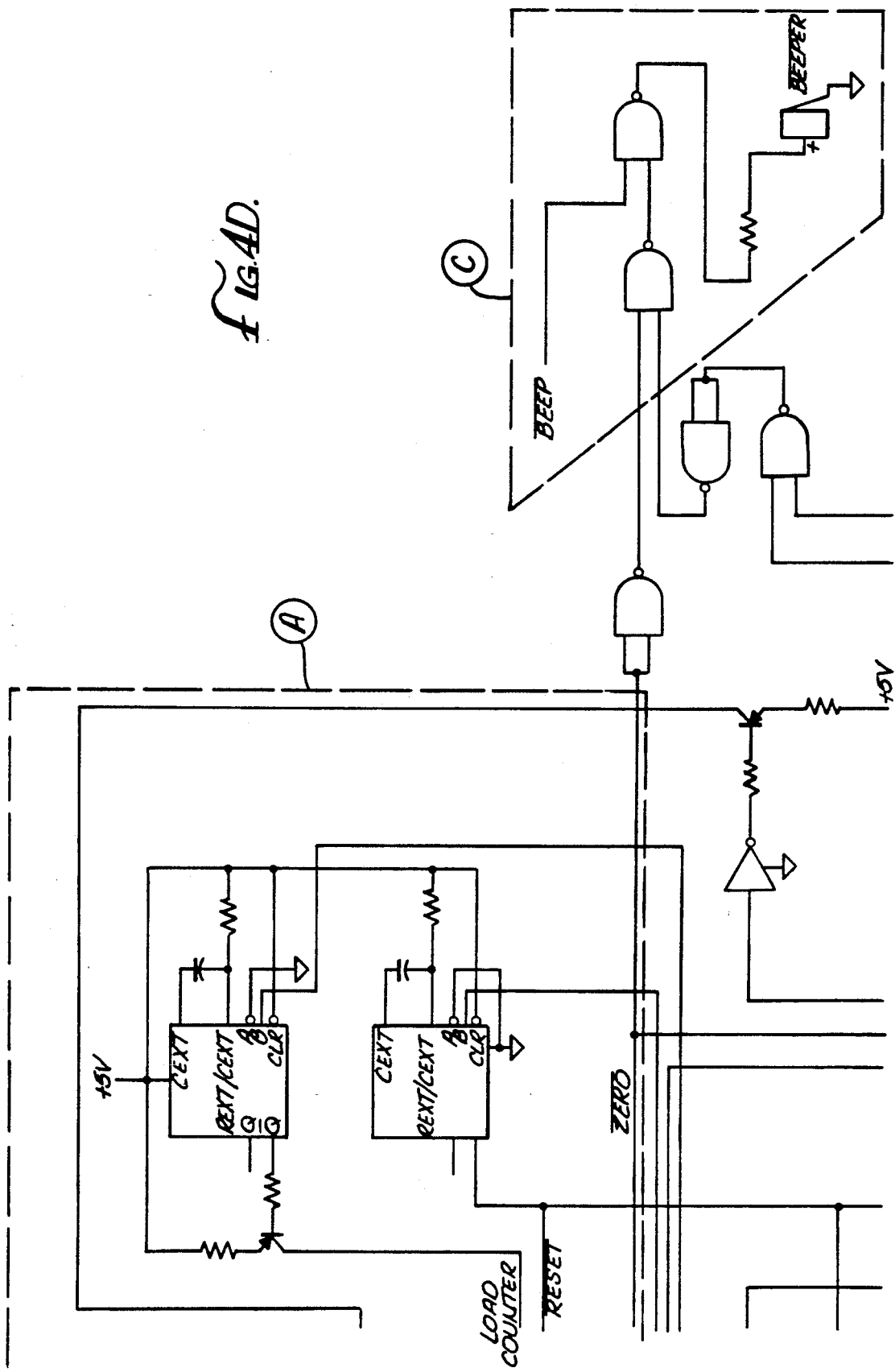

The electronic circuits for apparatus 2 are shown in generalized form in the block diagram of FIG. 3, with portions and additional elements shown in more detail in the schematic of FIG. 4. Referring primarily to FIG. 3, a power input line 30, which simply may be a cord to plug into a standard 110 or 220 volt line, is connected to a low voltage power supply 32 the output of which is delivered through line 34 to the various circuits as required. Line 30 is also connected to lamp fixture 10 through a relay 36 or equivalent. Relay 36 is deactivated (i.e., turned to the "off" position to de-energize fixture 10) through line 37, or a door switch 22, or through timer 46 or a control circuit 42. Thus, when switch 22 is open (i.e., door 18 of apparatus 2 is open), relay 36 is deactivated to deenergize fixture 10. Relay 36 is activated (i.e. turned to the "on" position to energize fixture 10) through line 47 connected to a keypad 48 which is mounted outside housing 4.

In particular, line 47 is connected to start/reset button 54 on keypad 48. Likewise, timer 46 and control circuit 42 are also connected to keypad 48. A key 56 selects timer 46 as the means by which relay 36 is deactivated, and hence by which fixture 10 is deenergized, following elapse of a set time entered by keys 52 on keypad 48 after the starts/reset button 54 is pushed. Keys 58, 60 on the other hand, select a variable memory 44 or a fixed memory 45, respectively of control circuit 42 as the means which will deactivate relay 36. Selecting fixed memory 44 results in relay 36 being deactivated, and hence fixture 10 being deenergized, when the total energy which is received by the specimen being irradiated (again, preferably a polynucleotide), as determined by photosensor 40 and a control circuit 48, corresponds to the predetermined value stored in variable memory 44. Alternatively, if key 60 is used to select variable memory 45, then a value can be stored in memory 45 through keys 52 on keypad 48, which will correspond to a selected total energy as determined by detector circuit 38. A display panel 50, typically a light emitting diode display, indicates the selection of keys 56, 58, 60 and the entries made on keys 62.

Figure 5A:
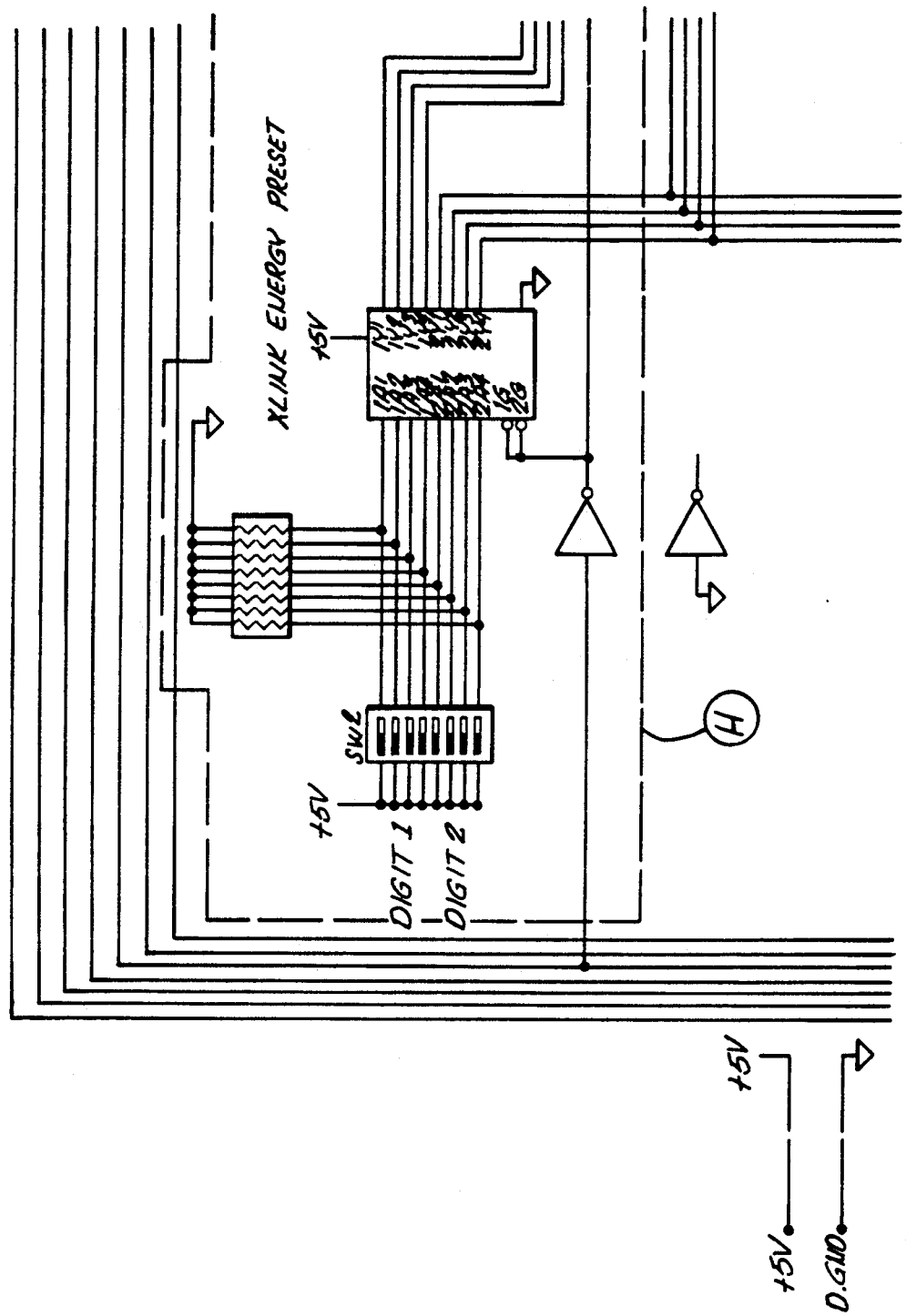
Figure 5C:
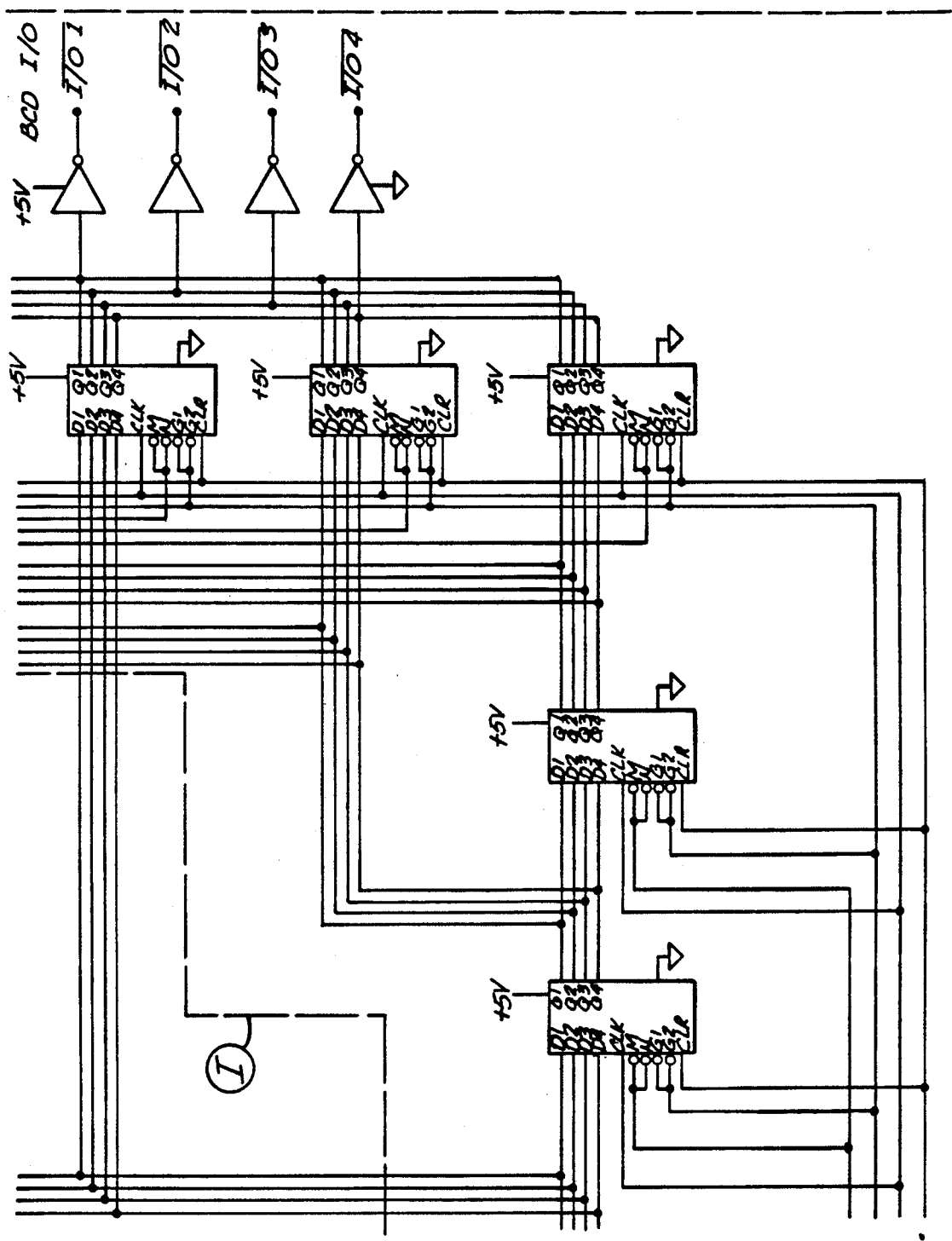

It is to be noted that the value in fixed memory 45 is predetermined by a manufacturer or a service person. This is accomplished through dip switches shown in FIGS. 5A and 5D, which are part of the fixed memory. Since the fixed memory value is more difficult to alter than the variable memory value, requiring access into compartment 16, and since it is retained in fixed memory 45 even if apparatus 2 is disconnected from a power line, it is a predetermined value.

A detailed schematic of most of the components of a circuit which corresponds to the block diagram of FIG. 3, is provided in FIGS. 4A-4D, and 5A-5D. In those Figures, block A represents a light emitting diode ("LED") control circuit. Block B is a current, to voltage, to frequency converter, which serves as energy detector 38, previously described. A beeper represented by C, additionally provides an audible indication when the UV dose equals that which has been selected or predetermined, or the elapsed time is equal to that selected, and the ultraviolet lamps are turned off. Timer 46 is essentially represented by block D. Block E is a control for relay 36, which responds then to the timer 46, control circuit 42, and door switch 22. A keypad decoder F serves to appropriately decode input on keypad 48. A non-numeric decoder G decodes non-numeric input on keypad 48, in particular the selection of the reset/start switch, the selection of the fixed or variable memory, and the selection of the timer. Block H forms part of fixed memory 45, and allows the predetermined value to be varied (in binary decimal code) through use of two sets of dip switches shown. Input storage and scroller, I, holds all digit values, including those for the fixed and variable memories, and the timer.

In practice of the method of the present invention using the apparatus 2 described above, it will be assumed that line 30 has already been connected to a suitable source of power, and that suitable UV lamps are already mounted in sockets 11. A specimen, typically DNA or RNA on a substrate, is placed on floor 9 of chamber 8, and door 18 is then closed. The user then decides if the UV irradiation is to be based solely on time or total UV dose, and if the latter, if a selected value is to be entered for the total UV dose or if the predetermined value which corresponds to the value stored in fixed memory 44 is to be used. If time is to be selected, switch 54 is pressed, and the desired total time entered by keys 52 on keypad 48. If a selected value of total UV dose is desired, then key 58 is pushed, and the desired total UV dose is entered by keys 52. If the predetermined total UV dose is desired, then key 60 is simply pressed. Following the foregoing operations, key 54 is pressed to start UV irradiation of the specimen. If any incorrect keys are pressed in the foregoing operation (and this can be monitored on the display 50), then key 54 can simply be pressed again and the operation repeated.

When key 54 is pressed to start UV irradiation, it will be noticed that nothing will happen unless door switch 22 is closed (i.e. door 18 is closed). Assuming door switch 22 is closed, then UV lamp fixture 10 will be energized for the selected total time, the selected total UV dose, or the predetermined UV dose, depending upon the selection made by keys 56, 58, and 60, as previously described. When either a selected or predetermined total UV dose are selected by the user, energy detector 38 provides a continuous indication to control circuit 42 of the total UV dose received on the floor 9 of chamber 8, based on the signal received from photodetector 40 adjacent floor 9. When the total UV dose indication of energy detector 38 corresponds to the predetermined or selected value (again, depending on the user's selection as described), relay 36 will be deactivated to de-energize UV lamp fixture 10 and turn off the UV lamps. Of course, if a desired UV exposure time has been selected by the user, then timer 46 will de-activate relay 36.

It will be seen from the above, that should the output of a UV lamp drop, or should a lamp totally fail, during a particular experiment, or over a number of experiments, the total energy received by a specimen will still be relatively accurately determined by the apparatus. Thus, if either the selected or predetermined total UV dose values are selected, reproducible results are obtained regardless of variations in UV flux from the UV lamps. Furthermore, a user is protected from UV exposure by chamber 8 and door switch 22.

With regard to the predetermined value stored in the fixed memory, it has been found that for the purposes of crosslinking a polynucleotide specimen to a nylon or nitrocellulose substrate generally, that a total UV dose of 1.29 KJ/m² produces good results, even with variations in the substrate and other conditions. This corresponds to a UV flux in the apparatus 2 of about 4300 microwatts per square centimetre, for 30 seconds.

Variations and modifications to the embodiments of the invention described above, are of course possible. Accordingly, the invention is not limited to those specific embodiments described.

TABLE 1

KEYPAD ENCODER
PCB wiring board
Bill Of Materials

| Item | Quantity | Reference | Part |
|---|---|---|---|
| 1 | 7 | U4, U5, U6, U7, U10, U11, U12 | MM74HC173N |
| 2 | 1 | U8 | CD4514BE |
| 3 | 1 | U9 | CD4078BE |
| 4 | 2 | SW2, SW3 | SW SPST DIP-8 CT2068 |
| 5 | 1 | U2 | MM74HC74N |
| 6 | 2 | C1, C2 | 0.10 MFD/50 V ECQ-V1H104JZ |
| 7 | 2 | U15, U14 | MM74HC244N |
| 8 | 1 | U13 | MM74HC04N |
| 9 | 2 | R1, R2 | RPACK, 10.0K 9S10E13A1002GL002 |
| 10 | 1 | U1 | MM74C922N |
| 11 | 1 | U3 | MM74HC125N |

TABLE 1-continued

KEYPAD ENCODER
PCB wiring board
Bill Of Materials

| Item | Quantity | Reference | Part |
|---|---|---|---|
| 12 | 1 | SW1 | KEYPAD |

TABLE 2

UV EXPOSURE UNIT, CONTROLLER
PCB WIRING
Bill Of Materials

| Item | Quantity | Reference | Part |
|---|---|---|---|
| 1 | 1 | C6 | 1.0 MFD/50 V ECQ-V1H105JZ |
| 2 | 3 | C8, C9, C12 | 10 MFD/25 V ECS-F1EE106K |
| 3 | 1 | C7 | 1000 pF/50 V COG 21RR510 |
| 4 | 4 | U18, U19, U20, U22 | MM74HC192N |
| 5 | 1 | U21 | CD4060BE |
| 6 | 3 | U23, U24, U31 | MM74HC00N |
| 7 | 2 | U25, U28 | MM74CH109N |
| 8 | 2 | U26, U27 | MM74HC04N |
| 9 | 2 | Q1, Q2 | 2N2907A |
| 10 | 2 | R12, R15 | 100 ohm 29SJ250 |
| 11 | 1 | R16 | 1.5K ohm 29SJ250 |
| 12 | 1 | C10 | 100 pF COG 21RD610 |
| 13 | 3 | C11, C13, C14 | 0.1 MFD/50 V ECQ-V1H104JZ |
| 14 | 1 | U30 | MM74HC123N |
| 15 | 2 | R14, R13 | 39K ohm 29SJ250 |
| 16 | 1 | SW4 | SPST |
| 17 | 2 | R8, R5 | 20K ohm pot EVM-CEGA01B24 |
| 18 | 1 | R7 | 470K ohm 29SJ250 |
| 19 | 4 | R6, R3, R18, R19 | 10K ohm 29SJ250 |

TABLE 3

| 20 | 2 | R4, R11 | 1K ohm 29SJ250 |
|---|---|---|---|
| 21 | 1 | R10 | 10 meg ohm 29SJ250 |
| 22 | 1 | R16 | 330 ohm 29SJ250 |
| 23 | 1 | BZ1 | BEEPER |
| 24 | 1 | C4 | *8 pF COG |
| 25 | 1 | C5 | *24 pF COG |
| 26 | 1 | R9 | 330K ohm 29SJ250 |
| 27 | 4 | D3, D1, D2, D4 | 1N4148 |
| 28 | 1 | R17 | 5.1K ohm 29SJ250 |
| 29 | 1 | U16 | OP-90GP |
| 30 | 1 | X1 | 32768 Hz, XTAL X32768-ND |
| 31 | 1 | U17 | AD537JH |
| 32 | 1 | DS1 | DISPLAY, LED |
| 33 | 1 | U29 | ICM72117AIPI |

I claim:

1. A method of irradiating a polynucleotide specimen on a substrate, the method comprising:
providing an apparatus having:
(a) a chamber having a repository for the substrate;
(b) an ultraviolet lamp fixture disposed within the chamber, which fixture carries an ultraviolet lamp to illuminate the repository;
(c) an energy detector which can provide an indication of the total ultraviolet dose received on the repository, the energy detector having:
   (i) a sensor disposed in a fixed location in the chamber, which provides a signal corresponding to the ultraviolet flux on the repository;
   (ii) a detector circuit connected to the sensor, so as to provide an indication of the total ultraviolet dose received on the repository based on the signal received from the sensor over time;
(d) a control circuit connected to the detector circuit and the lamp fixture, which control circuit can de-energize the lamp fixture upon detection of a selected or predetermined total ultraviolet dose by the energy detector;
the method further comprising placing the substrate carrying the polynucleotide into the chamber, then energizing the lamp fixture so that the polynucleotide specimen will be irradiated with ultraviolet radiation from the lamp until the control circuit de-energizes the lamp upon detection of the selected or predetermined total ultraviolet dose.

2. A method of irradiating a polynucleotide specimen on a substrate, the method comprising:
providing an apparatus having:
(a) a chamber which is substantially opaque to ultraviolet light and having:
   (i) a door allowing access to an interior of the chamber;
   (ii) a repository for the substrate;
(b) an ultraviolet lamp fixture disposed within the chamber, which fixture carries an ultraviolet lamp to illuminate the repository;
(c) an energy detector which can provide an indication of the total ultraviolet dose received on the repository, the energy detector having:
   (i) a sensor disposed in a fixed location in the chamber, which provides a signal corresponding to the ultraviolet flux on the repository;
   (ii) a detector circuit connected to the sensor, so as to provide an indication of the total ultraviolet dose received on the repository based on the signal received from the sensor over time;
(d) a control circuit connected to the detector circuit and the lamp fixture, which control circuit can de-energize the lamp fixture upon detection of a selected or predetermined total ultraviolet dose by the energy detector, the control circuit comprising:
   (i) a fixed memory which retains a fixed value corresponding to a fixed, predetermined total ultraviolet dose;
   (ii) a variable memory which allows for the selection of a variable value corresponding to a variable, selected total ultraviolet dose;
   (iii) a memory switch which engages either of the fixed or variable memories, such that the control circuit will de-energize the lamp fixture upon detection of the predetermined or selected total ultraviolet dose, respectively;
(e) a keypad on the outside of the chamber and connected to the control circuit and timer, the keypad carrying the memory switch and keys by which the variable value of the variable memory and timer setting can be selected;
the method further comprising placing the substrate carrying the polynucleotide in the chamber, entering on the keypad the setting of the memory switch, and further entering the setting of the variable memory if appropriate, then energizing the lamp fixture so that the polynucleotide specimen will be irradiated with ultraviolet radiation from the lamp until the control circuit de-energizes the lamp upon detection of the selected or predetermined total ultraviolet dose.

3. A method of irradiating a polynucleotide or protein specimen on a substrate, the method comprising:
   providing an apparatus having:
   (a) a chamber which is substantially opaque to ultraviolet light, and having:
      (i) a door allowing access to an interior of the chamber;
      (ii) a repository for the substrate;
   (b) an ultraviolet lamp fixture disposed within the chamber, which fixture carries an ultraviolet lamp to illuminate the repository;
   (c) an energy detector which can provide an indication of the total ultraviolet dose received on the repository, the energy detector having:
      (i) a sensor disposed in a fixed location in the chamber, which provides a signal corresponding to the ultraviolet flux on the repository;
      (ii) a detector circuit connected to the sensor, so as to provide an indication of the total ultraviolet dose received on the repository based on the signal received from the sensor over time;
   (d) a control circuit connected to the detector circuit and the lamp fixture, which control circuit can de-energize the lamp fixture upon detection of a selected or predetermined total ultraviolet dose by the energy detector; the method further comprising placing the substrate carrying the polynucleotide or protein into the chamber, then energizing the lamp fixture so that the polynucleotide specimen will be irradiated with ultraviolet light from the lamp until the control circuit de-energizes the lamp upon detection of the selected or predetermined total ultraviolet dose.

4. A method of irradiating a polynucleotide specimen on a substrate, the method comprising:
   providing an apparatus having:
   (a) a chamber which is substantially opaque to ultraviolet light, and having:
      (i) a door allowing access to an interior of the chamber;
      (ii) a repository for the substrate;
   (b) an ultraviolet lamp fixture disposed within the chamber, which fixture carries an ultraviolet lamp to illuminate the repository;
   (c) an energy detector which can provide an indication of the total ultraviolet dose received on the repository, the energy detector having:
      (i) a sensor disposed in a fixed location in the chamber, which provides a signal corresponding to the ultraviolet flux on the repository;
      (ii) a detector circuit connected to the sensor, so as to provide an indication of the total ultraviolet dose received on the repository based on the signal received from the sensor over time;
   (d) a control circuit connected to the detector circuit and the lamp fixture, which control circuit can de-energize the lamp fixture upon detection of a selected or predetermined total ultraviolet dose by the energy detector, the control circuit comprising:
      (i) a fixed memory which retains a fixed value corresponding to a fixed, predetermined total ultraviolet dose;
      (ii) a variable memory which allows for the selection of a variable value corresponding to a variable, selected total ultraviolet dose;
      (iii) a memory switch which engages either of the fixed or variable memories, such that the control circuit will de-energize the lamp fixture upon detection of the predetermined or selected total ultraviolet dose, respectively;
   (e) a timer connected to the lamp fixture, which timer can de-energize the lamp fixture upon elapse of a variable, selected period during which the lamp fixture is energized
   (f) a keypad on the outside of the chamber and connected to the control circuit and timer, the keypad carrying the memory switch and keys by
   which the variable value of the variable memory
   and timer setting can be selected; the method further comprising placing the substrate carrying the polynucleotide into the chamber, entering on the keypad the setting of either one of the memory switch and the timer, and further entering the setting of the variable memory or timer if appropriate, then energizing the lamp fixture so that the polynucleotide specimen will be irradiated with ultraviolet light from the lamp until the control circuit de-energizes the lamp upon detection of the selected or predetermined total ultraviolet dose.

5. A method of exposing a polynucleotide specimen to UV radiation, comprising
   providing apparatus having (a) a UV-opaque chamber, said chamber having a first region for disposing a specimen on a substrate, and having a second region for disposing a source of UV radiation, (b) a memory, and (c) a circuit for limiting an administered total UV dose to a desired UV dose, said circuit comprising (1) a UV sensor disposed at a fixed position in said chamber, (2) a first circuit coupled to said sensor capable of indicating a total UV dose received at said first region, and (3) a second circuit coupled to said first circuit and to said source of UV radiation, capable of de-energizing said source of UV radiation;
   placing the specimen on a substrate in said first region;
   retrieving from said memory either a first value corresponding to a predetermined desired total UV dose for said specimen or second value corresponding to a desired total UV dose which may be selected by an operator; and
   irradiating said first region with UV radiation under control of said circuit.

6. A method as in claim 5, wherein said UV radiation wavelength is between about 200 nanometers and about 290 nanometers.

* * * * *